Figure 1:
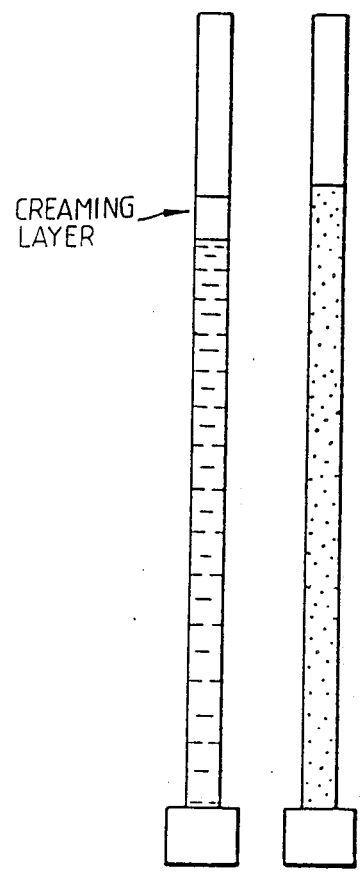

United States Patent [19]

Wretlind et al.

[11] Patent Number: 4,970,209

[45] Date of Patent: Nov. 13, 1990

[54] FAT EMULSIONS

[75] Inventors: Arvid K. J. Wretlind, Stockholm; Bengt M. Ajaxon, Uppsala, both of Sweden

[73] Assignee: International Nutritional Research Institute AB, Stockholm, Sweden

[21] Appl. No.: 334,800

[22] Filed: Apr. 3, 1989

Related U.S. Application Data

[63] Continuation of Ser. No. 923,938, Oct. 14, 1986, abandoned.

[30] Foreign Application Priority Data

Oct. 25, 1985 [SE] Sweden .............................. 85050474

[51] Int. Cl.$^5$ .............................................. A61K 31/55
[52] U.S. Cl. .................................................... 514/221
[58] Field of Search ......................................... 514/221

[56] References Cited

U.S. PATENT DOCUMENTS

| | | | |
|---|---|---|---|
| 2,055,083 | 9/1936 | Klein et al. | 424/178 |
| 3,793,450 | 2/1974 | Schnell | 424/195 |
| 4,073,943 | 2/1978 | Wretlind et al. | 424/178 |
| 4,158,707 | 6/1979 | Steffen et al. | 514/221 |
| 4,168,308 | 9/1979 | Wretlind et al. | 514/221 |
| 4,328,222 | 5/1982 | Schmidt | 514/221 |
| 4,411,894 | 10/1983 | Schrank et al. | 514/221 |

FOREIGN PATENT DOCUMENTS

| | | |
|---|---|---|
| 0144434 | 11/1084 | European Pat. Off. . |
| 0071995 | 8/1982 | European Pat. Off. . |
| 1249454 | 9/1967 | Fed. Rep. of Germany . |
| 2406621 | 1/1979 | Fed. Rep. of Germany . |
| 2938807 | 7/1982 | Fed. Rep. of Germany . |
| 3409793 | 9/1984 | Fed. Rep. of Germany . |
| 8600810 | 2/1986 | PCT Int'l Appl. . |
| 2091098 | 7/1982 | United Kingdom . |

OTHER PUBLICATIONS

International Search Report for Swedish Application No. 8505047-4, Ref. No. 129102/SAH.
Partial European Search Report for Application No. EP 86850372., Ref. No. 203815/SAH.

*Primary Examiner*—Stanley J. Friedman
*Attorney, Agent, or Firm*—Cushman, Darby & Cushman

[57] ABSTRACT

The invention concerns fat emulsion for intravenous adminstration for nutritive, diagnositic or therapeutic purposes, or for tissue culture and storage or organ transplants. According to the invention, the emulsion contains one or more substances preventing or retarding aggregation or agglutination ("creaming") when the emulsion is mixed with blood, serum or plasma.

14 Claims, 2 Drawing Sheets

CREAMING TESTS CARRIED
OUT IN WESTERGREN TUBES
LEFT TUBE: HEAVY CREAMING
RIGHT TUBE: NO CREAMING

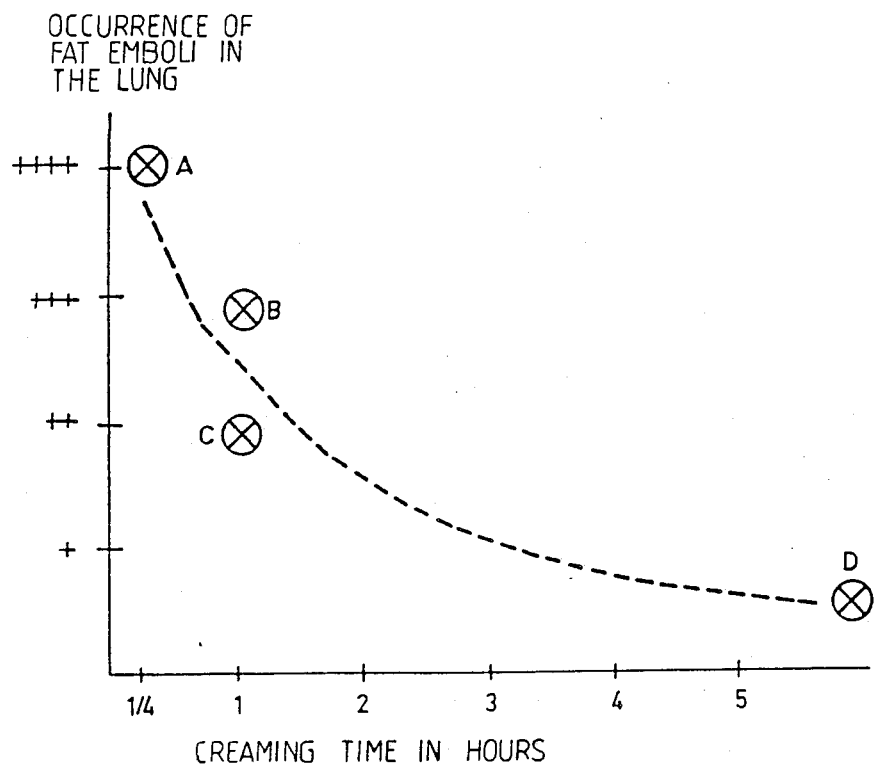

FAT EMULSIONS

This is a continuation of application Ser. No. 923,938, filed Oct, 24, 1986, now abandoned.

The present invention concerns a fat emulsion of the oil-in-water type. More specifically, the invention concerns a fat emulsion with or without vitamin and/or drug content for intravenous administration to humans or animals, or for tissue culture and storage of organ transplants. Special components can also be added to the emulsion giving it oxygen transporting properties.

Fat emulsions for nutritive or therapeutic use have been known for a long time and are i.a. described in SE patent No. 220,400, U.S. Pat. Nos. 4,073,943 and 4,168,308 and in many articles by i.a. Wretlind (J. Par. Ent. Nutr. 1981, 5, 230–235), Jeppson & Ljungberg (Acta Pharm. Toxicol 1975, 36, 312–320).

Solutions or fluids intended for intravenous administration must have special properties. They must be sterile and free from particles (see e.g. British Pharmacopoeia 1980, volume II, page 578 "Particulate matter"). Further, such solutions or fluids must be readily miscible with blood without occurrence of precipitations or turbidity or other signs of incompatibility in the process.

A special type of fluids intended for intravenous supply, the fat emulsions, is widely used. These fatty emulsions are utilized to add essential fatty acids and energy in the form of fat to patients who cannot eat normally, and therefore require an intravenous supply of nutrients.

Fat emulsions can also be used for the intravenous supply of water-insoluble but fat-soluble drugs (see U.S. Pat. Nos. 4,073,943 and 4,168,308). The lipophilic substance is then dissolved in the fat of the emulsion and the lipophilic substance can also partly be suspended in fat which is of animal or vegetable origin. In this way, the drug will be evenly distributed throughout the numerous extremely small fat droplets. The size of the droplets is generally smaller than 1 $\mu$m in diameter. It has been found that the effect of the compound when administered intravenously in the form of a fat emulsion will be as good as or superior to the injection into the bloodstream as an aqueous solution. Moreover, the fat emulsion is less harmful to the intima of the vessel walls and other tissues than the strongly acid or basic aqueous solutions which in many cases must be used to maintain the drug in solution.

Many different compositions of fat emulsions have been studied in order to obtain a greater stability at heat sterilization and storage (see for example DE-A No. 29 36 252, DE-A No. 29 38 807, and EP-A No. 2 7,995). However, it has been found that these emulsions are unstable when mixed with plasma or serum, and large aggregates of fat particles have been found to be formed. These aggregates can attain a size of 200 $\mu$m. As the aggregates have a lower density than serum or plasma, they will rapidly float to the surface, forming a layer, similar to cream, in a test tube. Accordingly, this reaction has been called "cream formation" or "creaming". The effect is described by several authors (LeVeen et al. Amer. Clin. Nutr. 1965, 16, 129–134; Forbes: J. Clin. Pathol. 1978, 31, 765–771; Hulman et al.: Lancet 1982, 25 Dec. 1426–1427). The occurrence of creaming is common.

It is obvious that said aggregates of fat particles may get stuck in the capillaries in various parts of the body, thereby blocking of the blood supply for variable periods of time to the tissues supplied with blood by these capillaries. Authors like Forbes (Clin. Pathol. 1978, 31, 765–771) and Levene et al. (Acta Paediatr. Scand. 1984, 73, 454–460) have maintained that these aggregates may rise to fat emboli in the patient's lungs, with fatal consequences in certain cases. The frequency of creaming varies with different emulsions and with serum or plasma from patients with different disease conditions. Some authors claim that fat emulsions should not be used if it is known or can be assumed that formation of aggregates or creaming might occur.

Before any fat emulsion can be accepted for intravenous use, a series of tolerance tests and other tests on animals must of course be carried out. Furthermore, it should also be shown that the emulsion has a good stability during long-time storage. One of the tests in vitro that also should be made concerns the stability of the emulsion when mixed with serum, plasma or blood. Only emulsions that can be mixed without aggregation or agglutination are acceptable. Testing is preferably performed as follows.

0.5 ml of serum or plasma from seriously ill patients is mixed in a test tube (55 × 12 mm) with 0.025 ml of a fat emulsion. Mixing is carried out thoroughly by reversing the test tube 10 times. The mixture is then transferred to a long glass tube (300 × 10.5 mm with an inside diameter of 2 mm, intended to be used for a sedimentation test according to Westergren). The amount of the mixture should be sufficient to reach a level corresponding to score 120 on the usual Westergren tubes (FIG. 1). The sample is stored for 7 hours at room temperature or at 37° C. If the sample is opalescent and lacks signs of creaming after a storage time of 3 hours, the stability of the emulsion can be considered as satisfactory.

Serum or plasma for the above-mentioned testing should be taken only, from the "critically ill patients". The serum's suitability for the test in vitro is demonstrated by the fact that creaming occurs within 5 min. with an emulsion composed according to Table 1.

TABLE 1

| Test emulsion | |
|---|---|
| Diazepam | 5 mg |
| Soybean oil | 150 mg |
| Myvacet ® (acetylated monoglycerides) | 50 mg |
| Egg yolk phospholipides | 12 mg |
| Glycerol | 22,5 mg |
| Distilled water to . | 1 ml |

Directed studies, performed after the phenomenon of creaming was described many years ago, have indicated that said creaming occurs in all examined types of fat emulsions when plasma or serum from "critically ill patients" is used.

It was not possible to quantitate the creaming effect in different emulsions by means of the technique used by previous investigators. Thus, it was only possible to judge whether or not creaming occured. Following numerous trials, it has now been found that the method described above could also be used to indicate, in quantitative terms, the creaming tendency in an emulsion or a patient serum. The tubes containing the mixture of serum or plasma and emulsion are then checked at regular intervals for 24 hours. Checking is preferably carried out by visual inspection or photographing after 15, 30, 60, 180 etc. minutes. The tendency to cream can easily be indicated in this way, preferably by giving the time when creaming can first be observed.

After the afore-mentioned method had been developed, great variations in creaming activity among different states of illness, on one hand, and different emulsions, on the other, could readily be demonstrated. The frequency of creaming with serum from patients in an intensive care unit in relation to points of time in the test scheme mentioned above is shown in Table 2.

TABLE 2

Occurrence of creaming in serum from patients in an intensive care unit using the fat emulsion described in Table 1

| Creaming after time indicated below. Time | Percentage of creaming samples |
|---|---|
| 15 minutes | 26 |
| 30 minutes | 41 |
| 1 hour | 49 |
| 2 hour | 60 |
| 3 hour | 66 |
| 4 hour | 71 |
| 5 hour | 75 |
| 6 hour | 76 |
| 7 hour | 78 |

Attempts to influence the creaming tendency of fat emulsions by using various additives have so far had little or no effect, and in many case an inferior emulsion stability was observed.

Experimental studies with serum from healthy animals, such as rat, have shown that various additives to the fat emulsion rather increased than decreased the tendency of creaming.

Since long, the possibilities of preventing creaming tendencies of fat emulsions by changing homogenization procedures, modifying the composition with alternative emulsifiers, etc. have been studied in many places. However, these early attempts were unsuccessful, and the conclusion was reached that creaming may occur in all types of fat emulsions. The issue of finding substances capable of preventing creaming has been taken up again, stimulated by the possibility mentioned above to quantitate the tendency of creaming. After systematic studies during many years, it has now quite unexpectedly been found that addition of certain substances indeed prevents creaming in the emulsions, without adversely affecting their stability. In several cases a considerable improvement of the stability has been obtained. Examples of compounds having these unexpected effects are glycerol, glycine, serine, phenylalanine, taurine, pelargonic acid, isovaleric acid, oleic acid and its salts, sodium edetate and urea, as shown in Table 3.

TABLE 3

Time when creaming occurs following mixing of serum with test emulsion alone (Table 1) or test emulsion in combination with various additives

| Test emulsion | Test emulsion + additive | Additive |
|---|---|---|
| 0.5 hours | <24 hours | Glycine |
| 0.5 hours | 7 hours | Serine |
| 0.5 hours | 7 hours | Phenylalanine |
| 0.25 hours | 5 hours | Taurine |
| 0.25 hours | 3 hours | Pelargonic acid |
| 0.25 hours | 24 hours | Isovaleric acid |
| 0.5 hours | 3 hours | Oleic acid |
| 0.25 hours | 7 hours | Sodium edetate |
| 0.25 hours | 4 hours | Urea |

The examples in the table are not limiting. The unexpected effects were obtained with compounds having a short carbon chain with one or two associated amino groups (e.g. amino acids and urea) or with short or long-chain fatty acids (pelargonic acid and oleic acid), i.e. with up to 20 carbon atoms and being carboxylic or sulfonic acids, optionally with one or more double bonds and optionally with at least one amino group in the molecule. The improvement of the stability is also seen in fluorocarbon emulsions used as oxygen carrying blood substitutes, in tissue culture, or for storage of organ transplants.

In the drawings, FIG. 1 schematically shows the creaming tests and their results. FIG. 2 is a diagram showing the relation between the creaming in vitro and the occurrence of fat emboli in the lungs of rats.

It has not been possible to give a purely chemical definition of the compounds active in preventing. The expert can, however, by using the earlier described test with serum or plasma and an emulsion with a predetermined composition in a simple way decide the potentially creaming preventive properties of a certain compound.

The composition of the fat emulsions is conventional in other respects and known from the afore-mentioned publications. Thus, they contain fats of animal or vegetable origin, such as fish oil, soybean oil, coconut oil or cottonseed oil, or triglycerides of a similar composition, emulsified in an aqueous phase. Monoglycerides of fatty acids and salts of fatty acids can also be included. Synthetic or natural phosfolipides from soybean or egg yolk are the primary emulsifiers; contributing emulsifiers may be include. The emulsions can also contain other components, for the adjustment of isotonic properties, preservatives, pH adjusting agents, various amino acids for widening the nutritional properties, etc. Agents for adjusting the isotonic properties may include carbohydrates such as fructose or glucose or sugar alcohols, such as sorbitol and glycerol, all adding energy as well. The amino acids can be essential as well as non-essential ones and are preferably included in an amount of 2-10 percent of the total weight of the emulsion. The emulsion sometimes also carries pharmacologically active agents as important components.

As indicated above, the emulsions can also be prepared in a known manner from organic fluorocarbon compounds with conventional auxiliary agents.

The preparation of these fat emulsions is also carried out in a conventional manner. Thus, the lipids with optional dissolved pharmacologically active substances are mixed with the aqueous phase, the preferred emulsifiers, auxiliary agents, and the compound or compounds preventing creaming in a suitable mixing device. Then the blend is homogenized to a desired particle size. The size of the particles must be less than the size of the red blood cells (about 8 μm) for an emulsion which is intended for intravenous injection, in order to secure that the particles may pass the capillaries without being trapped. Preferably, the particle size should be less than about 4 μm, and the main portion of the particles should have a diameter below 1 μm, suitably between 0.05 and 0.5 μm. The ways to adjust the emulsion to a suitable particle size is well-known to persons skilled in the art.

It is important that all components have a pharmacologically acceptable quality from the beginning and that the quality of the individual components is maintained throughout the whole preparation process. Thus, it is essential that the fat, the phospholipides and the monoglycerides are prepared and purified in a proper way, e.g. by suitable extraction and precipitation processes. They should be protected from contact with oxygen during preparation and storage to avoid the formation of oxidation products which may cause adverse reactions. This is of special importance when the emulsion is to be injected intravenously, in order to avoid side effects. Procedures for preparation of pharmacologically acceptable egg phospholipides and soybean oil are described i.a. in U.S. Pat. No. 3,169,094. Complying with the invention, the preparation and filling of emulsions must be performed in an inert atmosphere such as nitrogen gas.

The composItion of some test emulsions used in the investigations—the results of which are summarized in Table 3—is described in examples 1-9. Examples 10-14 describe emulsions for clinical use to which substances according to the invention have been added for the prevention of creaming. The enumeration and examples above are not limiting regarding the choice of substances. All percentage values are weight per cent unless otherwise indicated.

In addition to the afore-mentioned in vitro investigation, the improved resistance to creaming can be shown by the following experiment in vivo. Emulsions showing varying degrees of creaming with rat plasma were injected intravenously into rats weighing about 200 g. The injection was made via a catheter placed in a jugular vein, and a quantity of 2 ml was given during 20 min. The rat was sacrificed immediately after the injection, and organs were removed for sectioning and histopathological examination. The numbers of fat emboli in the organs was then found to be related to the times of creaming in the test in vitro, i.e. the greater the creaming ability, the larger the amount of fat emboli. FIG. 2 shows the ratio between fat emboli in the lungs of rats after infusion of fat emulsions with varyable tendency to cream and the creaming time.

EXAMPLE 1

| | |
|---|---|
| Diazepam | 0.5% |
| Soybean oil | 15% |
| Myvacet ® (acetylated monoglycerides) | 5% |
| Egg yolk phospholipides | 1.2% |
| Glycerol | 2.25% |
| Glycine | 0.25% |
| Sodium hydroxide solution 1M to pH | 7-10 |
| Sterile water to | 100 ml |

A crude emulsion was prepared from the constituents. It was subsequently passed through a high pressure homogenizer repeatedly to obtain an emulsion with the main portion of the particles being less than 1 μm. The emulsion was filled under nitrogen gas into injection vials of 10 ml and was sterilized at 121° C. during 20 min. in the usual manner.

When the creaming ability in serum was determined (see pages 4 and 5), the creaming time was on the average found to be prolonged more than 30 times that of a test emulsion lacking glycine for the prevention of creaming.

EXAMPLE 2

| | |
|---|---|
| Diazepam | 0.5% |
| Soybean oil | 15% |
| Myvacet ® (acetylated monoglycerides) | 5% |
| Egg yolk phospholipides | 1.2% |
| Glycerol | 2.25% |
| Glycine | 0.125% |
| Sodium edetate | 0.125% |
| Sodium hydroxide solution 1M to pH | 7-10 |
| Sterile water to | 100 ml |

An emulsion was prepared from the above constituents in the same way as in Example 1. The prolongation of the time until creaming occurred in serum was 48 times that of a test emulsion without glycine and sodium edetate.

EXAMPLE 3

| | |
|---|---|
| Diazepam | 0.5% |
| Soybean oil | 15% |
| Myvacet ® (acetylated monoglycerides) | 5% |
| Egg yolk Phospholipides | 1.2% |
| Glycerol | 2.25% |
| Glycine | 0.10% |
| Sodium hydroxide solution 1M to pH | 7-10 |
| Sterile water to | 100 ml |

An emulsion was prepared from the above constituents in the same way as in Example 1. The prolongation of the time until creaming occurred in serum was twice the time of a test emulsion without glycine.

EXAMPLE 4

| | |
|---|---|
| Diazepam | 0.5% |
| Soybean oil | 15% |
| Myvacet ® (acetylated monoglycerides) | 5% |
| Egg yolk phosphlipides | 1.2% |
| Glycerol | 2.25% |
| Serine | 0.25% |
| Sodium hydroxide solution 1M to pH | 7-10 |
| Sterile water to | 100 ml |

An emulsion was prepared from the above constituents in the same way as in Example 1. The prolongation of the time until creaming occurred in serum was about 40 times that observed with a test emulsion without serine.

EXAMPLE 5

| | |
|---|---|
| Diazepam | 0.5% |
| Soybean oil | 15% |
| Myvacet ® (acetylated monoglycerides) | 5% |
| Egg yolk phospholipides | 1.2% |
| Glycerol | 2.25% |
| Phenylalanine | 0.25% |
| Sodium hydroxide solution 1M to pH | 7-10 |
| Sterile water to | 100 ml |

An emulsion was prepared from the above constituents in the same way as in Example 1. The prolongation of the time until creaming occurred in serum was about 40 times that of a test emulsion without phenylalanine.

EXAMPLE 6

| | |
|---|---|
| Diazepam | 0.5% |
| Soybean oil | 15% |

| | |
|---|---|
| Myvacet ® (acetylated monoglycerides) | 5% |
| Egg yolk phospholipides | 1.2% |
| Glycerol | 2.25% |
| Taurine | 0.25% |
| Sodium hydroxide solution 1M to pH | 7-10 |
| Sterile water to | 100 ml |

An emulsion was prepared from the above constituents in the same way as in Example 1. The prolongation of the time to creaming occurred in serum was about 55 times that of a test emulsion without taurine.

EXAMPLE 7

| | |
|---|---|
| Diazepam | 0.5% |
| Soybean oil | 15% |
| Myvacet ® (acetylated monoglycerides) | 5% |
| Egg yolk phospholipides | 1.2% |
| Glycerol | 2.25% |
| Pelargonic acid | 0.25% |
| Sodium hydroxide solution 1M to pH | 7-10 |
| Sterile water to | 100 ml |

An emulsion was prepared from the above constituents in the same way as in Example 1. The prolongation of the time until creaming occurred in plasma was about 35 times that of a test emulsion without pelargonic acid.

EXAMPLE 8

| | |
|---|---|
| Diazepam | 0.5% |
| Soybean oil | 15% |
| Myvacet ® (acetylated monoglycerides) | 5% |
| Egg yolk phospholipides | 1.2% |
| Glycerol | 2.25% |
| Urea | 0.25% |
| Sodium hydroxide solution 1M to pH | 7-10 |
| Sterile water to | 100 ml |

An emulsion was prepared from the above constituents in the same way as in Example 1. The prolongation of the time until creaming occurred in plasma was about 40 times and in serum about 50 times compared with the time of a test emulsion without urea.

EXAMPLE 9

| | |
|---|---|
| Pregnanolone | 0.5% |
| Soybean oil | 20% |
| Myvacet ® (acetylated monoglycerides) | 6.7% |
| Egg yolk phospholipides | 1.2% |
| Glycerol | 2.25% |
| Glycine | 0.25% |
| Sodium hydroxide solution 1M to pH | 7-10 |
| Sterile water to | 100 ml |

An emulsion was prepared from the above constituents in the same way as in Example 1. The prolongation of the time until creaming occurred in serum was about 20 times that of a pregnanolone emulsion without glycine.

EXAMPLE 10

| | |
|---|---|
| Soybean oil | 10% |
| Egg yolk phospholipides | 1.2% |
| Glycerol | 2.25% |
| Glycine | 0.25% |
| Sodium hydroxide solution 1M to pH | 7-10 |
| Sterile water to | 100 ml |

An emulsion was prepared from the above constituents in the same way as in Example 1. The prolongation of the time until creaming occurred in plasma was 4 times in comparison with a test emulsion without glycine.

EXAMPLE 11

| | |
|---|---|
| Soybean oil | 10% |
| Egg yolk phospholipides | 1.2% |
| Glycerol | 2.25% |
| Phenylalanine | 0.25% |
| Sodium hydroxide solution 1M to pH | 7-10 |
| Sterile water to | 100 ml |

An emulsion was prepared from the above constituents in the same way as in Example 1. The prolongation of the time until creaming occurred in plasma was about 12 times in comparison with a test emulsion without phenylalanine.

EXAMPLE 12

| | |
|---|---|
| Soybean oil | 10% |
| Egg yolk phospholipides | 1.2% |
| Glycerol | 2.25% |
| Urea | 0.25% |
| Sodium hydroxide solution 1M to pH | 7-10 |
| Sterile water to | 100 ml |

An emulsion was prepared from the above constituents in the same way as in Example 1. The prolongation of the time until creaming occurred in plasma was about 10 times in comparison with a test emulsion without urea.

EXAMPLE 13

| | |
|---|---|
| Soybean oil | 10% |
| Egg yolk phospholipides | 1.2% |
| Glycerol | 2.25% |
| Serine | 0.25% |
| Sodium hydroxide solution 1M to pH | 7-10 |
| Sterile water to | 100 ml |

An emulsion was prepared from the above constituents in the same way as in Example 1. The prolongation of the time until creaming occurred in plasma was about 8 times compared with a test emulsion without serine.

EXAMPLE 14

| | |
|---|---|
| Soybean oil | 10% |
| Perfluorodecalin | 28% |
| Egg yolk phospholipides | 5% |
| Glycerol | 2.25% |
| Phenylalanine | 0.1% |
| Sodium hydroxide solution 1M to pH | 7-10 |
| Sterile water to | 100 ml |

An emulsion was prepared from the above constituents in the same way as in Example 1. At a shake test this emulsion was quite faultless after 96 hours, while oil drops as well as a bottom layer of perfluorodecalin could be noticed for a corresponding emulsion without phenylalanine as soon as 24 hours after the start. No creaming was obtained with serum, and a four-fold prolongation of the time for creaming with plasma was obtained in comparison with a test emulsion without phenylalanine.

We claim:

1. A fat emulsion, of an oil-in-water type, for parental administration, containing at least one compound having up to 20 carbon atoms, selected from the group consisting of urea, isovaleric acid, pelargonic acid and amino acid, which prevents creaming for at least three hours when the emulsion is mixed with human serum or plasma to a concentration of 1-10 percent by volume, the human serum or plasma being such that it creates creaming within 15 minutes when mixed with 1-10 percent by volume of an emulsion of the composition:

| Diazepam | 5 mg. |
| Soybean oil | 150 mg. |
| Acetylated monoglycerides | 50 mg. |
| Phospholipides from egg yolk | 12 mg. |
| Glycerol | 22.5 mg. |
| Distilled water to | 1 ml. |

2. Emulsion according to claim 1, wherein the compound is selected from the group consisting of glycine, serine, phenylalanine or taurine.

3. Emulsion according to claim 1, wherein said glycerol is present in a concentration of 2-30 percent by volume.

4. Emulsion according to claim 1, wherein said emulsion further includes a pharmacologically active agent.

5. Emulsion according to claim 1, wherein said emulsion further includes at least on perfluorinated hydrocarbon compound in a concentration of 2-30 percent by weight.

6. Emulsion according to claim 1, wherein said fat is selected from the group consisting of an animal fat, vegetable fat, the corresponding triglycerides of animal fat and the corresponding triglycerides of vegetable fat.

7. Emulsion according to claim 1, further including essential or non-essential amino acids in a concentration of 2-30 percent by weight.

8. A method for preventing creaming in fat emulsions for parenteral administration comprising:

mixing with a fat emulsion of an oil-in-water type, at least one compound having up to 20 carbon atoms selected from the group consisting of urea, isovaleric acid, pelargonic acid and amino acid, which prevents creaming for at least three hours when the emulsion is mixed with human serum or plasma to a concentration of 1-10 percent by volume the human serum or plasma being such that it creates creaming within 15 minutes when mixed with 1-10 percent by volume of an emulsion of the composition:

| Diazepam | 5 mg. |
| Soybean oil | 150 mg. |
| Acetylated monoglycerides | 50 mg. |
| Phospholipides from egg yolk | 12 mg. |
| Glycerol | 22.5 mg. |
| Distilled water to | 1 ml. |

9. The method of claim 8, wherein the compound is selected from the group consisting of glycine, serine, phenylalanine or taurine.

10. The method of claim 8, wherein said glycerol is present in a concentration of 2-30 percent by volume.

11. The method of claim 8, wherein said emulsion further includes a pharmacologically active agent.

12. The method of claim 8, wherein said emulsion further includes at least one perfluorinated hydrocarbon compound in a concentration of 2-30 percent by weight.

13. The method of claim 8, wherein said fat is selected from the group consisting of an animal fat, vegetable fat, and the corresponding triglycerides of animal fat and the corresponding triglycerides of vegetable fat.

14. The method of claim 8, further including essential or non-essential amino acids in a concentration of 2-10 percent by weight.

* * * * *